US007927382B2

(12) United States Patent
Audousset et al.

(10) Patent No.: US 7,927,382 B2
(45) Date of Patent: Apr. 19, 2011

(54) READY-TO-USE COMPOSITION FOR THE OXIDATION DYEING OF KERATIN FIBERS COMPRISING AT LEAST ONE FATTY SUBSTANCE, AT LEAST ONE OXIDATION CHOSEN FROM 4,5-DIAMINOPYRAZOLES AND ACID ADDITION SALTS THEREOF, AT LEAST ONE ADDITIONAL DYE PRECURSOR OTHER THAN THE AT LEAST ONE OXIDATION BASE, AT LEAST ONE OXIDIZING AGENT, AND OPTIONALLY AT LEAST ONE ALKALINE AGENT, AND PROCESSES AND KITS THEREWITH

(75) Inventors: Marie-Pascale Audousset, Asnieres (FR); Isabelle Schlosser, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,555

(22) Filed: Dec. 18, 2009

(65) Prior Publication Data
US 2010/0175203 A1  Jul. 15, 2010

Related U.S. Application Data

(60) Provisional application No. 61/150,930, filed on Feb. 9, 2009.

(30) Foreign Application Priority Data

Dec. 19, 2008 (FR) ...................................... 08 07320

(51) Int. Cl.
*A61Q 5/10* (2006.01)
*C07D 231/00* (2006.01)

(52) U.S. Cl. ............. 8/405; 8/406; 8/410; 8/411; 8/421; 8/435; 8/570; 8/580; 8/597; 8/604; 8/620; 548/371.7

(58) Field of Classification Search .............. 8/405, 406, 8/410, 411, 421, 435, 570, 580, 597, 604, 8/620; 548/371.7
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,845,293 A | 7/1989 | Junino et al. | |
| 5,021,066 A | 6/1991 | Aeby et al. | |
| 5,259,849 A | 11/1993 | Grollier et al. | |
| 5,364,414 A | 11/1994 | Lang et al. | |
| 5,817,155 A | 10/1998 | Yasuda et al. | |
| 6,010,541 A | 1/2000 | De La Mettrie et al. | |
| 6,074,439 A | 6/2000 | De La Mettrie et al. | |
| 6,129,770 A | 10/2000 | Deutz et al. | |
| 6,156,713 A | 12/2000 | Chopra et al. | |
| 6,165,444 A | 12/2000 | Dubief et al. | |
| 6,190,421 B1 | 2/2001 | Rondeau et al. | |
| 6,206,935 B1 | 3/2001 | Onitsuka et al. | |
| 6,238,653 B1 | 5/2001 | Narasimhan et al. | |
| 6,251,378 B1 | 6/2001 | Laurent et al. | |
| 6,260,556 B1 | 7/2001 | Legrand et al. | |
| 6,277,154 B1 | 8/2001 | Lorenz | |
| 6,277,155 B1 | 8/2001 | De La Mettrie et al. | |
| 6,365,136 B1 | 4/2002 | Lauscher et al. | |
| 6,423,100 B1 | 7/2002 | Lang et al. | |
| 6,447,552 B1 | 9/2002 | Golinski | |
| 6,645,258 B2 * | 11/2003 | Vidal et al. ........................ | 8/405 |
| 6,660,045 B1 | 12/2003 | Hoeffkes et al. | |
| 6,695,887 B2 | 2/2004 | Cottard et al. | |
| 6,800,098 B1 | 10/2004 | Allard et al. | |
| 7,135,046 B2 | 11/2006 | Audousset | |
| 7,153,331 B2 | 12/2006 | Desenne et al. | |
| 7,217,298 B2 | 5/2007 | Legrand et al. | |
| 7,285,137 B2 | 10/2007 | Vidal et al. | |
| 7,442,215 B2 | 10/2008 | Audousset et al. | |
| 7,458,993 B2 | 12/2008 | Cottard et al. | |
| 7,494,513 B2 | 2/2009 | Kravtchenko et al. | |
| 7,575,605 B2 | 8/2009 | Legrand | |
| 7,651,533 B2 | 1/2010 | Legrand | |
| 7,651,536 B2 | 1/2010 | Cottard et al. | |
| 7,766,977 B2 | 8/2010 | Cottard et al. | |
| 7,799,095 B2 | 9/2010 | Mario et al. | |
| 2003/0190297 A1 | 10/2003 | Narasimhan et al. | |
| 2003/0226217 A1 | 12/2003 | Bowes et al. | |

(Continued)

FOREIGN PATENT DOCUMENTS

CA      1 268 421      5/1990

(Continued)

OTHER PUBLICATIONS

French Search Report for FR 0807320, dated Sep. 15, 2009.

(Continued)

*Primary Examiner* — Eisa B Elhilo
(74) *Attorney, Agent, or Firm* — Finnegan, Henderson, Farabow, Garrett & Dunner

(57) ABSTRACT

Provided is a ready-to-use composition for the oxidation dyeing of keratin fibers, and for example human keratin fibers such as the hair, comprising: A) at least one fatty substance present in the ready-to-use composition in an amount of greater than or equal to 25% by weight relative to the total weight of the ready-to-use composition, B) at least one oxidation base chosen from 4,5-diaminopyrazoles and the acid addition salts thereof, C) at least one additional dye precursor other than the at least one oxidation base defined in B), D) at least one oxidizing agent, and optionally E) at least one alkaline agent. Also provided is a process comprising applying to the keratin fibers for a period of time sufficient to develop the desired coloring, the ready-to-use composition.

21 Claims, No Drawings

U.S. PATENT DOCUMENTS

| | | |
|---|---|---|
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2004/0234700 A1 | 11/2004 | Tchapian et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 A1 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 B1 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 449 512 | 8/2004 |
| EP | 1 486 195 | 12/2004 |
| EP | 1 488 781 B1 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |

| | | |
|---|---|---|
| WO | WO 2008/021641 | 2/2008 |
| WO | WO 2008/096497 | 8/2008 |
| WO | WO 2008/138844 | 11/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

English language abstract of DE 10 2006 012 575 A1, Feb. 8, 2007.
English language abstract of EP 1 166 749 B1, Jan. 22, 2002.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.

French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 8, 2010, in U.S. Appl. No. 12/642,473.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

READY-TO-USE COMPOSITION FOR THE OXIDATION DYEING OF KERATIN FIBERS COMPRISING AT LEAST ONE FATTY SUBSTANCE, AT LEAST ONE OXIDATION CHOSEN FROM 4,5-DIAMINOPYRAZOLES AND ACID ADDITION SALTS THEREOF, AT LEAST ONE ADDITIONAL DYE PRECURSOR OTHER THAN THE AT LEAST ONE OXIDATION BASE, AT LEAST ONE OXIDIZING AGENT, AND OPTIONALLY AT LEAST ONE ALKALINE AGENT, AND PROCESSES AND KITS THEREWITH

This application claims benefit of U.S. Provisional Application No. 61/150,930, filed Feb. 9, 2009. This application also claims benefit of priority under 35 U.S.C. §119 to French Patent Application No. 0807320, filed Dec. 19, 2008.

Disclosed herein is a ready-to-use composition for the oxidation dyeing of keratin fibers.

It is known practice to dye keratin fibers, and for example human hair, with dye compositions containing oxidation dyes, such as oxidation dye precursors and coloring modifiers.

Oxidation dye precursors, generally known as oxidation bases, may be initially colorless or weakly colored compounds which, in combination with oxidizing products, can give rise, via an oxidative condensation process, to colored and coloring compounds. They are, for example, compounds such as ortho- or para-phenylenediamines, ortho- or para-aminophenols and heterocyclic bases.

It is also known that it may be possible to vary the shades obtained with these oxidation bases by combining them with couplers or coloring modifiers, the latter, for example, being chosen from meta-diaminobenzenes, meta-aminophenols, meta-diphenols and certain heterocyclic compounds such as indole compounds.

The variety of the molecules involved as oxidation bases and couplers can make it possible to obtain a rich range of colors.

The "permanent" coloring obtained by virtue of these oxidation dyes, also called oxidation dyeing, should, moreover, meet at least one of a certain number of requirements. Thus, it should have no toxicological drawbacks, it should allow shades to be obtained in the desired strength, and it should show good fastness with respect to external attaches such as light, bad weather, washing, permanent-waving, perspiration and/or rubbing.

The dyes should also allow white hair to be covered and, finally, should be as nonselective as possible, i.e. they should make it possible to obtain the smallest possible differences in coloring right the way along the same keratin fiber, which is generally differently sensitized (i.e. damaged) between its tip and its root.

Many attempts have been made, in the hair-dyeing field, to improve the dyeing properties via, for example, adjuvants. However, the choice of these adjuvants can be tricky insofar as they should improve the dyeing properties of the dye compositions without being detrimental to the other properties of these compositions. For example, these adjuvants should not be detrimental to the keratin fiber-lightening properties and the coloring application properties.

One aspect of the present disclosure are novel ready-to-use compositions for the oxidation dyeing of keratin fibers which can avoid at least one of the drawbacks of the art. For example, disclosed herein are ready-to-use compositions for the oxidation dyeing of keratin fibers, which may have improved dyeing properties and which can be easy to mix and to apply, for example which do not run and which remain well localized at the point of application. The term "improved dyeing properties" is intended to mean for example an improvement in the level of strength/intensity and/or homogeneity of the dyeing.

Thus, provided is a ready-to-use composition for the oxidation dyeing of keratin fibers, and for example human keratin fibers such as the hair, comprising:

A) at least one fatty substance present in the ready-to-use composition in an amount of greater than or equal to 25% by weight relative to the total weight of the ready-to-use composition, B) at least one oxidation base chosen from 4,5-diaminopyrazoles and the acid addition salts thereof, C) at least one additional dye precursor other than the at least one oxidation base defined in B), D) at least one oxidizing agent, and optionally E) at least one alkaline agent.

The ready-to-use composition according to the present disclosure may have improved dyeing properties. For example, the ready-to-use composition of the disclosure may result in colorings which exhibit good strength and/or intensity and/or good homogeneity of the color along the fiber between the end and the root of the hairs (also referred to as coloring selectivity) and/or good chromaticity. The ready-to-use composition of the disclosure can be applied to the keratin fibers without difficulty, and without running. This ready-to-use composition also can make it possible to obtain reduced degradation of the keratin fibers during the dyeing process.

Finally, the colorings obtained via the ready-to-use compositions of the disclosure may be color fast, and may withstand at least one of the various external attacks that keratin fibers may be subjected to.

Provided herein is also a process for dyeing keratin fibers, comprising applying to the keratin fibers the ready-to-use composition according to the disclosure for a sufficient time to develop the desired coloration Further provided is a multicompartment kit for application of the various components of the ready-to-use composition of the disclosure.

As has been mentioned, the ready-to-use composition of the disclosure comprises at least one fatty substance.

The term "fatty substance" is intended to mean an organic compound which is insoluble in water at normal temperature (25° C.) and at atmospheric pressure (760 mmHg) (solubility less than 5% and such as less than 1%, further such as less than 0.1%). They may have, in their structure, a sequence of at least two siloxane groups or at least one hydrocarbon-based chain containing at least six carbon atoms. In addition, fatty substances can be soluble in organic solvents under the same temperature and pressure conditions, for instance in chloroform, ethanol, benzene or decamethylcyclopentasiloxane.

According to the present disclosure, the at least one fatty substance is for example chosen from fatty substances other than fatty acids. The at least one fatty substance is for example chosen from lower alkanes, fatty alcohols, fatty acid esters, fatty alcohol esters, oils, such as nonsilicone mineral, plant, animal and synthetic oils, nonsilicone waxes and silicones.

According to at least one embodiment, the alcohols, esters and fatty acids have for example at least one saturated or unsaturated, linear or branched hydrocarbon-based groups containing 6 to 30 carbon atoms, which are optionally substituted, such as with at least one hydroxyl group (for example 1 to 4). If they are unsaturated, these compounds may comprise one to three conjugated or nonconjugated carbon-carbon double bonds.

With regard to the lower alkanes, the latter for example may contain from 6 to 16 carbon atoms and can be linear or branched, optionally cyclic. By way of example, the alkanes may be chosen from hexane and dodecane, isoparaffins such as isohexadecane and isodecane.

As nonsilicone oils that can be used in the ready-to-use composition of the disclosure, mention may, for example, be made of:

hydrocarbon-based oils of animal origin, such as perhydrosqualene;

hydrocarbon-based oils of plant origin, such as liquid triglycerides of fatty acids containing from 6 to 30 carbon atoms, for instance triglycerides of heptanoic acid or octanoic acid or alternatively, for example, sunflower oil, corn oil, soya oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names MIGLYOL® 810, 812 and 818 by the company Dynamit Nobel, jojoba oil, shea butter oil;

linear or branched hydrocarbons containing more than 16 carbon atoms, of mineral or synthetic origin, such as liquid paraffins, petroleum jelly, liquid petroleum jelly, polydecenes, hydrogenated polyisobutene such as PARLEAM®;

partially hydrocarbon-based fluoro oils; as fluoro oils, mention may also be made of perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or else the bromoperfluorooctyl sold under the name FORALKYL® by the company Atochem; nonafluoromethoxybutane and nonafluoroethoxyisobutane; perfluoromorpholine derivatives, such as 4-trifluoromethyl perfluoromorpholine sold under the name PF 5052® by the company 3M.

The fatty alcohols that can be used as fatty substances in the ready-to-use composition of the disclosure are nonoxyalkylenated, saturated or unsaturated, linear or branched, and contain 6 to 30 carbon atoms, and for example from 8 to 30 carbon atoms; mention may be made of cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

The nonsilicone wax(es) that can be used in the ready-to-use composition of the disclosure is (are) chosen for example from carnauba wax, candelilla wax, esparto grass wax, paraffin wax, ozokerite, plant waxes such as olive wax, rice wax, hydrogenated jojoba wax and the absolute waxes of flowers such as the essential wax of blackcurrant blossom sold by the company Bertin (France), animal waxes, for instance beeswaxes or modified beeswaxes (cerabellina); other waxes or waxy starting materials that can be used according to the disclosure are for example marine waxes such as the product sold by the company Sophim under the reference name M82, polyethylene waxes and polyolefin waxes in general.

The esters are esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being for example greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyle erucate; oleyl erucate; ethyl and isopropyl palmitates, 2-ethylhexyl palmitate, 2-octyldecyl palmitate, alkyl myristates such as isopropyl myristate, butyl myristate, cetyl myristate, 2-octyldodecyl myristate, mirystyl myristate or stearyl myristate, hexyl stearate, butyl stearate, isobutyl stearate; dioctyl malate, hexyl laurate, and 2-hexyldecyl laurate.

According to at least one embodiment, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may for example be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisonoanonate; and polyethylene glycol distearates.

Among the esters mentioned above, further non-limiting mention can be made of ethyl palmitate, isopropyl palmitate, myristyl palmitate, cetyl palmitate, stearyl palmitate, 2-ethylhexyl palmitate, 2-octyldecyl palmitate, alkyl myristates such as isopropyl myristate, butyl myristate, cetyl myristate or 2-octyldodecyl myristate, hexyl stearate, butyl stearate, isobutyl stearate; dioctyl malate, hexyl laurate, 2-hexyldecyl laurate, isononyl isononanate or cetyl octanoate.

The ready-to-use composition may also comprise, as fatty ester, sugar esters and diesters of $C_6$-$C_{30}$, and such as $C_{12}$-$C_{22}$, fatty acids. As used herein, the term "sugar" is intended to mean oxygen-bearing hydrocarbon-based compounds containing several alcohol functions, with or without aldehyde or ketone functions, and which contain at least four carbon atoms. These sugars may be monosaccharides, oligosaccharides or polysaccharides.

As suitable sugars, mention may, for example, be made of sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen for example from esters or mixtures of esters of sugars described previously and of linear or branched, saturated or unsaturated $C_6$-$C_{30}$, such as $C_{12}$-$C_{22}$, fatty acids. If they are unsaturated, these compounds may comprise one to three conjugated or nonconjugated carbon-carbon double bonds.

The esters according to at least one embodiment may also be chosen from mono-, di-, tri- and tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, oleo-palmitate, oleo-stearate and palmito-stearate mixed esters.

Non-limiting mention can be made of monoesters and diesters and such as sucrose, glucose or methylglucose mono- or dioleates, stearates, behenates, oleopalmitates, linoleates, linolenates and oleostearates.

By way of example, mention may be made of the product sold under the name GLUCATE® DO by the company Amerchol, which is a methylglucose dioleate.

By way of examples of esters or mixtures of esters of sugar and of fatty acid mention may also be made of the following:
- the products sold under the names F160, F140, F110, F90, F70, SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referenced B370 and corresponding to sucrose behenate formed from 20% monoester and 80% diester-triester-polyester;
- the sucrose mono-dipalmito-stearate sold by the company Goldschmidt under the name TEGOSOFT® PSE.

The silicones that can be used in the ready-to-use composition of the present disclosure are for example volatile or nonvolatile, cyclic, linear or branched silicones which can be unmodified or modified with organic groups, having a viscosity from $5 \times 10^{-6}$ to $2.5$ m$^2$/s at 25° C., and such as from $1 \times 10^{-5}$ to $1$ m$^2$/s at 25° C.

The silicones that can be used in accordance with the disclosure may be in the form of oils, waxes, resins or gums.

For example, the silicone is chosen from polydialkylsiloxanes, such as polydimethylsiloxanes (PDMS), and organo-modified polysiloxanes comprising at least one functional group chosen from poly(oxyalkylene) groups, amino groups and alkoxy groups.

The organopolysiloxanes are defined in greater detail in Walter Noll's "Chemistry and Technology of Silicones" (1968), Academie Press. They can be volatile or nonvolatile.

When they are volatile, the silicones are for example chosen from those having a boiling point ranging from 60° C. to 260° C., and further for example are chosen from:
- cyclic polydialkylsiloxanes containing from 3 to 7, such as from 4 to 5 silicon atoms. They are for example octamethylcyclotetrasiloxane sold for example under the name VOLATILE SILICONE® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Mention may also be made of cyclocopolymers of the dimethylsiloxane/methylalkylsiloxane type, such as VOLATILE SILICONE® FZ 3109 sold by the company Union Carbide, of formula:

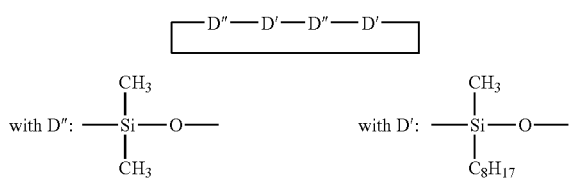

Mention may also be made of mixtures of cyclic polydialkylsiloxanes with organosilicon compounds, such as the mixture of octamethylcyclotetrasiloxane and tetratrimethyl-silylpentaerythritol (50/50) and the mixture of octamethylcyclotetrasiloxane and oxy-1,1'-bis(2,2,2'2',3,3'-hexatrimethyl-silyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold for example under the name SH 200 by the company Toray Silicone. Silicones belonging to this category are also described in the article published in Cosmetics and Toiletries, Vol. 91, Jan. 76, pp. 27-32, Todd & Byers "Volatile Silicone fluids for cosmetics".

Nonvolatile polydialkylsiloxanes, polydialkylsiloxane gums and resins, polyorganosiloxanes modified with organo-functional groups above, and also mixtures thereof, for example, are used.

These silicones are for example chosen from polydialkylsiloxanes, among which mention may be made of polydimethylsiloxanes containing trimethylsilyl end groups. The viscosity of the silicones is measured at 25° C. according to ASTM standard 445 Appendix C.

Among these polydialkylsiloxanes, mention may be made, in a nonlimiting manner, of the following commercial products:
- the SILBIONE® oils of the 47 and 70 047 series or the MIRASIL® oils sold by Rhodia, for instance the oil 70 047 V 500 000;
- the oils of the MIRASIL® series sold by the company Rhodia;
- the oils of the 200 series from the company Dow Corning, such as DC200 with a viscosity of 60,000 mm$^2$/s;
- the VISCASIL® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

In this category of polydialkylsiloxanes, mention may also be made of the products sold under the names ABIL WAX® 9800 and 9801 by the company Goldschmidt which are poly(C$_1$-C$_{20}$)dialkylsiloxanes.

The silicone gums that can be used in accordance with the disclosure are for example polydialkylsiloxanes, such as polydimethylsiloxanes with high number-average molecular masses ranging from 200,000 to 1,000,000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane, tridecane, and mixtures thereof.

Products that can for example be used in accordance with the disclosure are mixtures such as:
- mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
- mixtures of a polydimethylsiloxane gum and of a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and for example of a PDMS gum and of a PDMS oil, such as the product SF 1236 from the company General Electric.

The product SF 1236 is a mixture of an SE 30 gum defined above, having a viscosity of 20 m²/s, and an SF 96 oil, having a viscosity of 5×10⁻⁶m²/s. This product for example contains 15% SE 30 gum and 85% SF 96 oil.

The organopolysiloxane resins that can be used in accordance with the disclosure are crosslinked siloxane systems containing the following units:

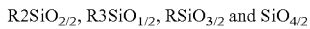

R2SiO$_{2/2}$, R3SiO$_{1/2}$, RSiO$_{3/2}$ and SiO$_{4/2}$ wherein R represents an alkyl containing 1 to 16 carbon atoms. Among these products, non-limiting mention can be made of those wherein R denotes a C$_1$-C$_4$ lower alkyl group, such as methyl.

Among these resins, mention may be made of the product sold under the name Dow Corning 593 or those sold under the names Silicone Fluid SS 4230 and SS 4267 by the company General Electric, and which are silicones of dimethyl/trimethyl siloxane structure.

Mention may also be made of the trimethylsiloxysilicate type resins sold for example under the names X22-4914, X21-5034 and X21-5037 by the company Shin-Etsu.

The organomodified silicones that can be used in accordance with the disclosure are silicones as defined above and comprising in their structure at least one organofunctional group attached via a hydrocarbon-based group.

Besides the silicones described above, the organomodified silicones may be polydiarylsiloxanes, such as polydiphenylsiloxanes, and polyalkylarylsiloxanes functionalized with the organofunctional groups mentioned previously.

The polyalkylarylsiloxanes are chosen for example from linear and/or branched polydimethyl/methylphenylsiloxanes and polydimethyl/diphenylsiloxanes with a viscosity ranging from 1×10⁻⁵ to 5×10⁻² m²/s at 25° C.

Among these polyalkylarylsiloxanes, mention may, by way of example, be made of the products sold under the following names:
- the SILBIONE® oils of the 70 641 series from Rhodia;
- the oils of the RHODORSIL® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Among the organomodified silicones, mention may be made of polyorganosiloxanes comprising:
- polyethyleneoxy and/or polypropyleneoxy groups optionally comprising C$_6$-C$_{24}$ alkyl groups, such as the products known as dimethicone copolyol sold by the company Dow Corning under the name DC 1248 or the oils SILWET® L 722, L 7500, L 77 and L 711 from the company Union Carbide, and the (C$_{12}$)alkylmethicone copolyol sold by the company Dow Corning under the name Q2 5200;
- substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, C$_1$-C$_4$ aminoalkyl groups;
- alkoxylated groups such as the product sold under the name Silicone Copolymer F-755 by SWS Silicones, and ABIL WAX® 2428, 2434 and 2440 by the company Goldschmidt.

In some embodiments, the at least one fatty substance is neither oxyalkylenated nor glycerolated.

For example, the at least one fatty substance is chosen from compounds that are liquid and compounds that arepasty at ambient temperature and at atmospheric pressure.

For example, the at least one fatty substance is a compound that is liquid at a temperature of 25° C. and at atmospheric pressure.

The at least one fatty substance is for example chosen from lower alkanes, fatty alcohols, fatty acid esters, fatty alcohol esters, oils, such as nonsilicone mineral, plant and synthetic oils, and silicones.

According to at least one embodiment, the at least one fatty substance is chosen from liquid petroleum jelly, polydecenes and liquid esters of fatty acids and of fatty alcohols, and mixtures thereof; for example, the at least one fatty substance of the ready-to-use composition according to the disclosure is non-silicone-based.

Alkanes or hydrocarbons and silicones will for example in some embodiments be chosen.

The ready-to-use composition according to the disclosure comprises at least 25% of at least one fatty substance. For example, the amount of fatty substance can range from 25% to 80%, such as from 25% to 65%, further such as from 30% to 55% by weight relative to the total weight of the ready-to-use composition.

The ready-to-use composition according to the disclosure comprises at least one oxidation base of the 4,5-diaminopyrazole type.

The at least one 4,5-diaminopyrazole oxidation base is for example chosen from compounds of formula (I) and the addition salts thereof:

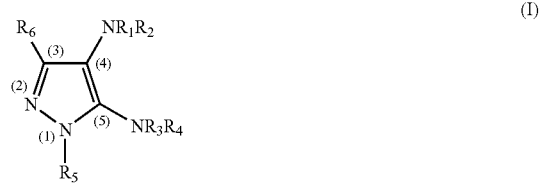

(I)

wherein:
R$_1$, R$_2$, R$_3$, R$_4$ and R$_5$, which may be identical or different, represent a hydrogen atom; or a C$_1$-C$_6$ alkyl radical which is unsubstituted or substituted with at least one substituent chosen from OR, with R, which may be identical or different, representing a hydrogen atom or an alkyl radical, and R$_6$ is a hydrogen atom or a C$_1$-C$_6$ alkyl radical.

The compounds of formula (I) may be optionally salified with strong inorganic acids such as, for example, HCl, HBr, HI, H$_2$SO$_4$ or H$_3$PO$_4$, or organic acids such as, for example, acetic acid, lactic acid, tartaric acid, citric acid, succinic acid, benzenesulfonic acid, para-toluenesulfonic acid, formic acid or methanesulfonic acid.

They may also be in the form of solvates, for example, a hydrate, or a solvate of a linear or branched alcohol such as ethanol or isopropanol.

By way of examples of 4,5-diaminopyrazole derivatives that can be used according to the disclosure, mention may be made of the compounds described in German Patent Nos. 38 43 892 and 41 33 957 and PCT Patent Application Publication Nos. WO 94/08969, WO 94/08970, French Patent No. 2 733 749 and German Patent No. 195 43 988, for instance 4,5-diamino-1-methylpyrazole, 4,5-diamino-1-(2-hydroxyethyl)pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole, and addition salts thereof.

Further non-limiting mention can be made of 4,5-diamino-1-(2-hydroxyethyl)-1H-pyrazole and addition salts thereof, such as 4,5-diamino-1-(2-hydroxyethyl)-1H-pyrazole sulfate, of formula below:

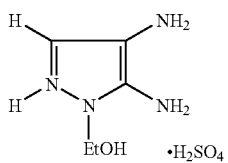

The amount of 4,5-diaminopyrazole oxidation bases and/or acid addition salts thereof may range from 0.005% to 10% by weight, relative to the total weight of the reay-to-use composition, such as from 0.05% to 1.5%.

In addition to the 4,5-diaminopyrazole oxidation base, the ready-to-use composition may contain at least one additional dye precursor.

The at least one additional dye precursor is chosen from oxidation bases other than 4,5-diaminopyrazoles and couplers.

The oxidation base(s) (other than the 4,5-diaminopyrazole) that can be used in the context of the present disclosure is (are) chosen from those conventionally known in oxidation dyeing, and among which mention may for example be made of ortho- and para-phenylenediarnines, double bases, ortho- and para-aminophenols, heterocyclic bases and also the acid addition salts.

These oxidation bases may for example be cationic.

The para-phenylenediamines that can be used in the context of the disclosure may for example be chosen from the compounds of formula (II) below and acid addition salts thereof:

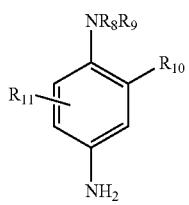

wherein:
$R_8$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ alkyl radical substituted with a nitrogenous, phenyl or 4'-aminophenyl group;

$R_9$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ alkyl radical substituted with a nitrogenous group;

$R_8$ and $R_9$ may also form, with the nitrogen atom which bears them, a nitrogenous heterocycle containing 5 or 6 ring members, optionally substituted with at least one group chosen from alkyl, hydroxyl and ureido;

$R_{10}$ represents a hydrogen atom, a halogen atom such as a chlorine atom, or a $C_1$-$C_4$ alkyl, sulfo, carboxyl, $C_1$-$C_4$ monohydroxyalkyl or $C_1$-$C_4$ hydroxyalkoxy, $C_1$-$C_4$ acetylaminoalkoxy, $C_1$-$C_4$ mesylaminoalkoxy or $C_1$-$C_4$ carbamoylaminoalkoxy radical;

$R_{11}$ represents a hydrogen or halogen atom or a $C_1$-$C_4$ alkyl radical.

Among the nitrogenous groups in formula (II) above, mention may for example be made of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Among the para-phenylenediamines of formula (II) above, mention may for example be made of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 4-N,N-bis(β-hydroxyethyl)amino-2-methylaniline, N,N-bis(β-hydroxyethyl-para-phenylenediamine, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 2-methyl-1-N-β-hydroxyethyl-para-phenylenediamine, and acid addition salts thereof.

Among the para-phenylenediamines of formula (II) above, non-limiting mention can be made of para-phenylenediamine, para-toluylenediamine, 2-isopropyl-para-phenylenediamine, 2-β-hydroxyethyl-para-phenylenediamine, 2,6-dimethyl-para-phenylenediamine, 2,6-diethyl-para-phenylenediamine, 2,3-dimethyl-para-phenylenediamine, 2-chloro-para-phenylenediamine and N,N-bis(β-hydroxyethyl)-para-phenylenediamine, and acid addition salts thereof.

Further non-limiting mention may be made of para-phenylenediamine, para-toluylenediamine, N,N-bis(β-hydroxyethyl)-para-phenylenediamine, and acid addition salts thereof.

According to the disclosure, the term "double bases" is intended to mean compounds comprising at least two aromatic rings on which amino and/or hydroxyl groups are carried.

Among the double bases that can be used as oxidation bases in the ready-to-use composition in accordance with the disclosure, mention may for example be made of the compounds of formula (III) below and acid addition salts thereof:

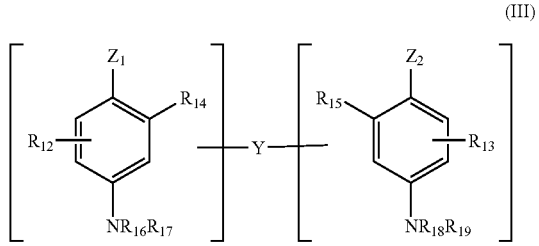

(III)

wherein:

$Z_1$ and $Z_2$, which may be identical or different, represent a hydroxyl or —$NH_2$ radical that may be substituted with a $C_1$-$C_4$ alkyl radical or with a linker arm Y;

the linker arm Y represents a linear or branched alkylene chain containing from 1 to 14 carbon atoms, that may be interrupted or terminated with at least one nitrogenous group and/or with at least one heteroatom such as oxygen, sulfur or nitrogen atom, and optionally substituted with at least one hydroxyl or $C_1$-$C_6$ alkoxy radical;

$R_{12}$ and $R_{13}$ represent a hydrogen or halogen atom, a $C_1$-$C_4$ alkyl, $C_1$-$C_4$ monohydroxyalkyl, $C_2$-$C_4$ polyhydroxyalkyl or $C_1$-$C_4$ aminoalkyl radical, or a linker arm Y;

$R_{14}$, $R_{15}$, $R_{16}$, $R_{17}$, $R_{18}$ and $R_{19}$, which may be identical or different, represent a hydrogen atom, a linker arm Y or a $C_1$-$C_4$ alkyl radical;

provided that the compounds of formula (III) comprise only one linker arm Y per molecule.

Among the nitrogenous groups in formula (III) above, mention may for example be made of amino, mono($C_1$-$C_4$) alkylamino, di($C_1$-$C_4$)alkylamino, tri($C_1$-$C_4$)alkylamino, monohydroxy($C_1$-$C_4$)alkylamino, imidazolinium and ammonium radicals.

Among the double bases of formulae (III) above, further mention may for example be made of N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and acid addition salts thereof.

Among these double bases of formula (III), even further non-limiting mention may be made of N,N'-bis(β-hydroxyethyl)-N,N'-bis(4'-aminophenyl)-1,3-diaminopropanol, 1,8-bis(2,5-diaminophenoxy)-3,5-dioxaoctane or acid addition salts thereof.

The para-aminophenols that can be used in the context of the dislcosure may for example be chosen from the compounds of formula (IV) below and acid addition salts thereof:

(IV)

wherein:

$R_{20}$ represents a hydrogen atom, a halogen atom such as fluorine, or a $C_1$-$C_4$ alkyl, $C_1$-$C_4$ monohydroxyalkyl, ($C_1$-$C_4$)alkoxy($C_1$-$C_4$)alkyl, $C_1$-$C_4$ aminoalkyl or a ($C_1$-$C_4$)hydroxyalkyl($C_1$-$C_4$)aminoalkyl radical;

$R_{21}$ represents a hydrogen atom or a halogen atom such as fluorine, or a $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl or ($C_1$-$C_4$)alkoxy($C_1$-$C_4$)alkyl radical.

Among the para-aminophenols of formula (IV) above, mention may for example be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and acid addition salts thereof.

Further non-limiting mention may be made of para-aminophenol and 4-amino-3-methylphenol.

The ortho-aminophenols that can be used as oxidation bases in the context of the present disclosure are for example chosen from 2-aminophenol, 2-amino-1-hydroxy-5-methylbenzene, 2-amino-1-hydroxy-6-methylbenzene and 5-acetamido-2-aminophenol, and acid addition salts thereof.

Among the heterocyclic bases that can be used as oxidation bases in the ready-to-use composition in accordance with the disclosure, mention may for example be made of pyridine derivatives, pyrimidine derivatives and pyrazole derivatives, and acid addition salts thereof.

Among the pyridine derivatives, mention may for example be made of the compounds described, for example, in Great Britain Patent Nos. 1 026 978 and 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and acid addition salts thereof.

Among the pyrimidine derivatives, mention may for example be made of the compounds described, for example, in German Patent No. 2 359 399 or Japanese Patent Nos. 88-169 571 and 91-10659 or PCT Patent Application Publication No. WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in French Patent Application Publication No. 2 750 048 and among which mention may be made of pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine, 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-imidazolylpropylaminopyrazolo[1,5-a]pyrimidine; addition salts thereof and tautomeric forms thereof, when a tautomeric equilibrium exists.

As pyrazole derivatives, mention may also be made of diamino-N,N-dihydropyrazolopyrazolones, and for example those described in French Patent Application Publication No. 2 886 136, such as the following compounds and addition salts thereof: 2,3-diamino-6,7-dihydro-1H,5H-pyrazolo[1,2- a]pyrazol-1-one, 2-amino-3-ethylamino-6,7-dihydro-1H, 5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo [1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a] pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

2,3-diamino-6,7-dihydro-1H,5H-pyrazolo[1,2-a]pyrazol-1-one and/or an addition salt thereof can, for example, be used.

As cationic oxidation bases that can be used in the ready-to-use compositions according to the disclosure, mention may, for example, be made of the following compounds: para-phenylenediamines as for example described in French Patent Application Publication Nos. 2 766 177 and 2 766 178, para-aminophenols as described, for example, in French Patent Application Publication Nos. 2 766 177 and 2 766 178, ortho-phenylenediamines as described, for example, in French Patent Application Publication Nos. 2 782 718, 2 782 716 and 2 782 719, ortho-aminophenols or double bases which are cationic, such as derivatives of bis(aminophenyl) alkylenediamine type, described in French Patent Application Publication No. 2 766 179, and also cationic heterocyclic bases, these compounds bearing at least one quaternary nitrogen atom.

For example, the cationic oxidation bases that can be used in the ready-to-use compositions according to the disclosure are cationic para-phenylenediamines.

For example, some embodiments consist in using cationic oxidation bases of para-phenylenediamine structure, at least one of the amine functions of which is a tertiary amine bearing a pyrrolidine ring, the molecule having at least one quaternized nitrogen atom. Such bases are, for example, described in European Patent Application Publication No. 1 348 695.

The ready-to-use composition according to the disclosure for example comprises a total amount of oxidation bases ranging from 0.0005% to 12% by weight, relative to the total weight of the ready-to-use composition. For example, it comprises a total amount of oxidation bases ranging from 0.005% to 8% by weight, and such as from 0.05% to 5% by weight, relative to the total weight of the ready-to-use composition.

The at least one coupler that can be used in the ready-to-use composition according to the disclosure is (are) that (those) for example conventionally used in oxidation dyeing compositions, i.e. meta-aminophenols, meta-phenylenediamines, meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the acid addition salts thereof.

These couplers are for example chosen from 2,4-diamino-1-(β-hydroxyethyloxy)benzene, 2-methyl-5-aminophenol, 5-N-(β-hydroxyethyl)amino-2-methyiphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo-[3,2-c]-1,2,4-triazole and 2,6-dimethylpyrazolo-[1,5-b]-1,2,4-triazole, and acid addition salts thereof.

The ready-to-use composition according to the disclosure may comprise a total amount of couplers ranging from 0.0001% to 15% by weight, relative to the total weight of the composition. For example, it may comprise a total amount of couplers ranging from 0.001% to 10% by weight, and such as from 0.01% to 8% by weight, relative to the total weight of the ready-to-use composition.

The oxidation bases and couplers may be present in the ready-to-use compositions of the disclosure in the form of addition salts, and such as in the form of acid addition salts.

The acid addition salts that can be used in the context of the disclosure are for example chosen from hydrochlorides, hydrobromides, sulfates, citrates, succinates, tartrates, lactates, acetates, alkyl sulfates and alkyl sulfonates.

When the oxidation bases or the couplers comprises at least one carboxylic acid or sulfonic acid function, base addition salts can be envisioned. The base addition salts that can be used in a context of the ready-to-use compositions of the dislcosure are then for example those obtained with sodium hydroxide, potassium hydroxide, aqueous ammonia or amines.

According to at least one embodiment of the disclosure, the ready-to-use composition comprises at least one additional oxidation base and at least one coupler.

According to at least one embodiment, the at least one additional oxidation base is chosen from para-aminophenols and heterocyclic bases and also the acid addition salts thereof.

The ready-to-use composition in accordance with the present disclosure comprises at least one oxidizing agent.

The at least one oxidizing agent is chosen, for example, from peroxides such as hydrogen peroxide and urea peroxide, bromates and ferricyanides of alkali metals, and persalts such as perborates, percarbonates and persulfates. As oxidizing agent, mention may also be made of at least one oxidoreduction enzymes such as laccases, peroxidases and 2-electron oxidoreductases (such as uricase), optionally in the presence of their respective donor or cofactor.

Further non-limiting mention may be made of hydrogen peroxide. This oxidizing agent is for example constituted of aqueous hydrogen peroxide, the titer of which may vary, for example, from 1 to 40 volumes, and such as from 5 to 40 volumes.

The amount of the at least one oxidizing agent of the ready-to-use composition of the disclosure for example ranges from 0.1% to 20% by weight, and such as from 0.5% to 10% by weight relative tothe total weight of the ready-to-use composition.

The ready-to-use composition of the disclosure for example comprises at least one alkaline agent. The at least one alkaline agent is, for example, chosen from aqueous ammonia, alkali metal carbonates and bicarbonates, and for example sodium carbonate and bicarbonate and potassium carbonate and bicarbonate, alkanolamines such as mono-, di- and triethanolamines, and derivatives thereof, hydroxyalkylamines and ethylenediamines which are oxyethylenated and oxypropylenated, sodium hydroxide, potassium hydroxide, amino acids, and for example basic amino acids such as arginine and lysine, and the compounds of formula (V) below

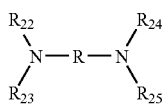

(V)

wherein:
R is a propylene residue optionally substituted with a hydroxyl group or a $C_1$-$C_4$ alkyl radical;
$R_{22}$, $R_{23}$, $R_{24}$ and $R_{25}$, which may be identical or different, represent a hydrogen atom, a $C_1$-$C_4$ alkyl radical or a $C_1$-$C_4$ hydroxyalkyl radical.

According to at least one embodiment, the ready-to-use composition comprises a small amount of aqueous ammonia, or even no aqueous ammonia. According to this embodiment, the ready-to-use composition for example comprises at least one alkanolamine, such as monoethanolamine or 2-amino-2-methyl-1-propanol.

According to at least one embodiment, the ready-to-use composition comprises as alkaline agent at least one organic amine, for example at least one alkanolamine. When the ready-to-use composition comprises more than one alkaline agents including an alkanolamine and ammonium hydroxides or their salts, the amount of organic amine(s) are for example higher than the amount of ammonia.

The amount of the at least one alkaline agent of the ready-to-use composition of the disclosure for example ranges from 0.01% to 30% by weight, and such as from 0.1% to 20% by weight relative to the total weight of the ready-to-use composition.

The ready-to-use composition in accordance with the disclosure may also comprise at least one direct dye that may for example be chosen from nitrobenzene dyes, azo direct dyes, methine direct dyes, and addition salts thereof. These direct dyes may be of nonionic, anionic or cationic nature.

The ready-to-use composition may also comprise other compounds constituting the dyeing medium. This dyeing medium may comprise water or a mixture of water and at least one cosmetically acceptable organic solvent, which is for example water-soluble.

As examples of organic solvents, mention may for example be made of alcohols such as ethyl alcohol, isopropyl alcohol, benzyl alcohol and phenylethyl alcohol, or glycols or glycol ethers such as, for example, monomethyl, monoethyl or monobutyl ethers of ethylene glycol, propylene glycol or its ethers, such as, for example, propylene glycol monomethyl ether, butylene glycol, hexylene glycol, dipropylene glycol and also diethylene glycol alkyl ethers such as, for example, diethylene glycol monoethyl ether or diethylene glycol monobutyl ether. The solvents may then be present in an amount ranging from 0.01% to 35% by weight, and such as from 0.1% to 25% by weight, relative to the total weight of the ready-to-use composition.

For example, the ready-to-use composition of the disclosure comprises water. Further for example, the amount of water may range from 10% to 70%, such as from 20% to 55% relative to the total weight of the ready-to-use composition.

The ready-to-use composition in accordance with the disclosure may also comprise at least one adjuvant conventionally used in hair-dyeing compositions.

The term "adjuvant" is intended to mean an additive other than the above mentioned compounds.

As examples of the at least one adjuvant that can be used, mention may be made of anionic, cationic, nonionic, amphoteric or zwitterionic surfactants, or mixtures thereof; anionic, cationic, nonionic, amphoteric or zwitterionic polymers, inorganic or organic thickeners, and for example anionic, cationic, nonionic and amphoteric associative polymeric thickeners, other than the associative celluloses according to the disclosure; antioxidants or reducing agents; penetrating agents; sequestering agents; fragrances; buffers; dispersing agents; conditioning agents such as, for example, volatile or nonvolatile silicones, which may be modified or unmodified; film-forming agents; ceramides, preservatives; opacifiers; and antistatic agents.

The above adjuvants are for example present in an amount, for each of them, ranging from 0.01% to 20% by weight, relative to the weight of the ready-to-use composition.

For example, the ready-to-use composition of the dislcosure comprises at least one surfactant.

For example, the at least one surfactant is chosen from nonionic surfactants and from anionic surfactants.

The anionic surfactants are for example chosen from the salts (for example alkali metal salts, such as sodium salts, ammonium salts, amine salts such as the amino alcohol salts, and alkaline-earth metal salts, for instance the magnesium salt) of the following compounds:
alkyl sulfates, alkyl ether sulfates, alkylamido ether sulfates, alkylaryl polyether sulfates, monoglyceride sulfates;
alkylsulfonates, alkylamidesulfonates, alkylarylsulfonates, α-olefin sulfonates, paraffin sulfonates;
alkyl phosphates, alkyl ether phosphates;
alkylsulfosuccinates, alkyl ether sulfosuccinates, alkylamidesulfosuccinates, alkylsulfosuccinamates;
alkylsulfoacetates;
acylsarcosinates; acylisethionates and N-acyltaurates;
salts of fatty acids such as oleic acid, ricinoleic acid, palmitic acid and stearic acid, coconut oil acid and hydrogenated coconut oil acid;
alkyl-D-galactoside uronic acid salts;
acyllactylates;
salts of polyoxyalkylenated alkyl ether carboxylic acids, of polyoxyalkylenated alkylaryl ether carboxylic acids and of polyoxyalkylenated alkylamido ether carboxylic acids, such as those containing from 2 to 50 ethylene oxide groups;
and mixtures thereof.

It should be noted that the alkyl or acyl radical of these various compounds for example contains from 6 to 24 carbon atoms, and such as from 8 to 24 carbon atoms, the aryl radical for example denoting a phenyl or benzyl group.

The nonionic surfactants are for example chosen from monooxyalkylenated and polyoxyalkylenated, monoglycerolated and polyglycerolated nonionic surfactants. The oxyalkylene units are for example oxyethylene or oxypropylene units, or a combination thereof, such as oxyethylene units.

As examples of oxyalkylenated nonionic surfactants, mention may be made of:
oxyalkylenated ($C_8$-$C_{24}$)alkylphenols,
saturated or unsaturated, linear or branched, oxyalkylenated $C_8$-$C_{30}$ alcohols,
saturated or unsaturated, linear or branched, oxyalkylenated $C_8$-$C_{30}$ amides,
esters of saturated or unsaturated, linear or branched $C_8$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils, and
condensates of ethylene oxide and/or of propylene oxide, inter alia, alone or as mixtures.

The surfactants contain a number of moles of ethylene oxide and/or of propylene oxide of from 1 to 50, such as from 2 to 30. For example, the nonionic surfactants do not comprise any oxypropylenated units.

In accordance with at least one embodiment of the disclosure, the oxyalkylenated nonionic surfactants are chosen from oxyethylenated $C_8$-$C_{30}$ and oxyethylenated $C_{18}$-$C_{30}$ alcohols.

As examples of monoglycerolated or polyglycerolated nonionic surfactants, non-limiting mention may be made of monoglycerolated or polyglycerolated $C_8$-$C_{40}$ alcohols.

For example, the monoglycerolated or polyglycerolated $C_8$-$C_{40}$ alcohols are chosen from compounds of the formula below:

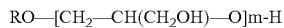

wherein R represents a linear or branched $C_8$-$C_{40}$, such as $C_8$-$C_{30}$, alkyl or alkenyl radical, and m represents a number ranging from 1 to 30 and such as from 1 to 10.

As examples of compounds that are suitable in the context of the disclosure, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, non-limiting mention can be made of the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

For example, the at least one surfactant present in the ready-to-use composition of the disclosure is a nonionic surfactant.

The at least one surfactant content in the ready-to-use composition of the disclosure represents for example from 0.1% to 50% by weight, such as from 0.5% to 30% by weight, relative to the weight of the ready-to-use composition.

Of course, those skilled in the art will take care to select the optional adjuvant(s) mentioned above in such a way that the effective properties intrinsically associated with the ready-to-use compositions of the disclosure are not, or are not substantially, impaired by the adjuvant(s).

The pH of the ready-to-use composition in accordance with the disclosure for example ranges from 3 to 12 y, such as from 5 to 11, further such as from 7 to 11. It may be adjusted to the desired value via acidifying or basifying agents that are normally used in the dyeing of keratin fibers, or alternatively via conventional buffer systems.

The at least one alkaline agent is, for example, those previously described.

Among the acidifying agents, mention may be made, as examples, of inorganic or organic acids such as hydrochloric acid, ortho-phosphoric acid, carboxylic acids such as tartaric acid, citric acid or lactic acid, or sulfonic acids.

The ready-to-use composition according to the disclosure may be in various forms, such as in the form of liquids, creams or gels, or in any other form suitable for dyeing keratin fibers, and for example human hair.

Disclosed herein is a process wherein the ready-to-use composition according to the present disclosure as defined above is applied to the keratin fibers. The color may be revealed at acidic, neutral or alkaline pH and the at least one oxidizing agent may be added just at the time of use or it may be used simultaneously with or sequentially to the other compounds of the ready-to-use composition of the disclosure.

After a leave-in time which for example ranges from 1 to 60 minutes, such as from 5 to 45 minutes, the keratin fibers are rinsed, optionally washed with shampoo and rinsed again, and then dried.

The ready-to-use composition according to the dislcosure may result from the mixing of at least two compositions, and for example of two or three compositions, such as including an oxidizing composition comprising at least one oxidizing agent as defined above. One of the compositions may be anhydrous.

The present disclosure also relates to a multi-compartment kit, comprising
- a first compartment containing a composition comprising at least one fatty substance,
- a second compartment containing at least one oxidation base chosen from 4,5-diaminopyrazoles and acid addition salts thereof, at least one additional dye precursor other than the at least one oxidation base chosen from 4,5-diaminopyrazoles, and the optionally at least one alkaline agent, and
- a third compartment containing at least one oxidizing agent, and optionally at least one fatty substance.

In some embodiments, the ready-to-use composition comprising the at least one fatty substance may be anhydrous. For the purpose of the dislcosure, the term "anhydrous composition" is intended to mean a cosmetic composition which has a water content of less than 5% by weight, such as less than 2% by weight, and further such as less than 1% by weight, relative to the weight of the ready-to-use composition. It should be noted that this water is for example bound water, such as the water from the crystallization of the salts or traces of water absorbed by the starting materials used in the preparation of the ready-to-use compositions according to the disclosure.

Also provided is a multi-compartment kit, comprising
- a first compartment containing a composition comprising at least one fatty substance and at least one oxidizing agent, and
- a second compartment containing a composition comprising at least one oxidation base chosen from 4,5-diaminopyrazoles and the acid addition salts thereof, the at least one additional dye precursor other than the at least one oxidation base chosen from 4,5-diaminopyrazoles, and, optionally, at least one alkaline agent.

This kit may be fitted with at least one applicator for delivering the desired mixture onto the hair, such as the applicators described in French Patent Application Publication No. 2 586 913.

Further provided is a multi-compartment kit, comprising
- a first compartment containing a composition comprising at least one fatty substance, at least one oxidation base chosen from 4,5-diaminopyrazoles and acid addition salts thereof, at least one dye precursor other than the at least one oxidation base chosen from 4,5-diaminopyrazoles, and, optionally, at least one alkaline agent, and
- a second compartment containing at least one oxidizing agent.

The examples which follow are intended to illustrate the disclosure without, however, limiting the scope thereof.

EXAMPLE

The following compositions were prepared:

| Composition 1 | Concentration (g %) |
|---|---|
| DISTEARDIMONIUM HECTORITE | 3 |
| OCTYLDODECANOL | 11.5 |
| GLYCOL DISTEARATE | 8 |
| LIQUID PETROLEUM JELLY | 64.5 |
| PROPYLENE CARBONATE | 1 |
| LAURETH-2 | 1 |
| POLYSORBATE 21 | 11 |

| Composition 2 | Concentration (g %) |
|---|---|
| DIETHYLENETRIAMINEPENTACETIC ACID, PENTASODIUM SALT AS AN AQUEOUS SOLUTION AT 40% | 1 |
| SODIUM METABISULFITE | 0.7 |
| MONOETHANOLAMINE | 14.5 |
| 1-METHYL-2,5-DIAMINOBENZENE | 0.87 |
| PARA-AMINOPHENOL | 0.464 |
| 1-METHYL-2-HYDROXY-4-AMINOBENZENE | 3.25 |
| 1H-PYRAZOLE-1-ETHANOL, 4,5-DIAMINO, SULFATE | 4 |
| NATROSOL 250 HHR (hydroxyethylcellulose) | 1.5 |
| HEXYLENE GLYCOL | 3 |
| DIPROPYLENE GLYCOL | 3 |
| ETHYL ALCOHOL | 8.25 |
| PROPYLENE GLYCOL | 6.2 |
| ASCORBIC ACID | 0.25 |
| WATER | Qs 100 g |

| Composition 3 | Concentration (g %) |
|---|---|
| DIETHYLENETRIAMINEPENTACETIC ACID, PENTASODIUM SALT AS AN AQUEOUS SOLUTION AT 40% | 0.15 |
| HYDROGEN PEROXIDE IN SOLUTION AT 50% (200 VOL. AQUEOUS HYDROGEN PEROXIDE) | 12 |
| SODIUM STANNATE | 0.04 |
| SODIUM PYROPHOSPHATE | 0.03 |
| LIQUID PETROLEUM JELLY | 20 |
| HEXADIMETHRINE CHLORIDE (AM at 60% in water) | 0.25 |
| POLYQUATERNIUM-6 (AM at 40% in water) | 0.5 |
| GLYCEROL | 0.5 |
| CETYLSTEARYL ALCOHOL (C16/C18 30/70) | 8 |
| OXYETHYLENATED (33 EO) CETYLSTEARYL ALCOHOL | 3 |
| PROTECTED OXYETHYLENATED (4 EO) RAPESEED ACID AMIDE at 92.3% in water | 1.3 |
| VITAMIN E | 0.1 |
| PHOSPHORIC ACID | Qs pH 2.2 |
| WATER | QS 100 g |

The three compositions were mixed at the time of use, in the following proportions: 10 g of composition 1 with 4 g of composition 2 and 16 g of composition 3. The mixture was applied to locks of natural grey hair containing 90% of white hairs, in a proportion of 10 g of mixture per 1 g of hair. After a leave-in time of 30 min, the hair was rinsed, washed with a standard shampoo and dried.

The hair coloring was evaluated visually.

| Example 1 | Light brown with a vivid red glint |
|---|---|

Example 2

The following compositions were prepared (quantity expressed in g)

|  | A1 (comparative) | A2 (inventive) |
|---|---|---|
| isopropyle Myristate | 52 | 87 |
| Oleth-10 | 10 | 10 |
| Disteardimonium hectorite | 2.25 | 2.25 |
| propylene Carbonate | 0.75 | 0.75 |
| Water | 35 | — |

Composition B (in g)

| copper sulphate 2-(4,5-diamino-1H-pyrazol-1-yl ethanol | 3.4833 |
|---|---|
| 2-methyl 5-aminophenol | 1.7835 |
| Hydroxyethyl cellulose (Natrosol 250 HHR) | 1.5 |
| Glycol Dipropylene | 3 |
| Glycol Hexylene | 3 |
| Propylene glycol | 6.2 |
| Monoethanolamine | 15.04 |
| Ethanol | 8.25 |
| Reducers, sequestering agents | Qs |
| Water | Qs 100 |

Composition C (in g)

| hydrogen Peroxide | 6 |
|---|---|
| cetearylic Alcohol | 2.28 |
| Ceteareth-25 | 0.57 |
| Glycerin | 0.5 |
| Trideceth-2 MEA carboxamide | 0.85 |
| Stabilising agents, sequestering agents | Qs |
| phosphoricque Acid | Qs pH = 2 |
| Water | Qs 100 |

The composition A1 and A2 were each separately mixed together with the compositions B and C at the time of use in the following proportions: 10 g of composition A1 or A2 with 4 g of composition B and 15 g of composition C.

The resulting mixtures were then applied on natural hair with 90% of white hair and on permed hair with 90% of white hair and strongly sensitized hair hair (SA42), at the rate of 14.5 g of mixture for 1 g of hair. After a leave-on time of 30 minutes, the hair was rinsed, washed with a standard shampoo and dried.

The colour of the hair was determined by using the Datacolor SF600X Spectraflash (illuminant D65, angle 10°, specular components included).

According to this system, L* indicates the lightness. The lower the value of L*, the more intense the color of the hair.

The chromaticity coordinates were expressed by the parameters a* and b*, a* indicating the axis of red/green shades and b the axis of yellow/blue shades.

Chromaticity:

For each colored lock, the chromaticity was evaluated from the following formula:

$$C^* = \sqrt{(a^*)^2 + (b^*)^2}$$

| Type of hair | Mixture | a* | b* | C* |
|---|---|---|---|---|
| BN | A1 + B + C | 35.17 | 24.73 | 43.00 |
|  | A2 + B + C (invention) | 37.63 | 26.39 | 45.96 |
| BP | A1 + B + C | 35.17 | 24.87 | 43.07 |
|  | A2 + B + C (invention) | 37.37 | 25.48 | 45.23 |

In both cases, the mixture obtained with the composition A2 led to a color more chromatic than the mixture obtained with the composition A1.

Selectivity:

The selectivity of the color on hair was also evaluated

The selectivity of the coloration is the variation of the color between natural colored hair and the highly sensitized (permed) colored hair. The selectivity ΔE was calculated from the following formula:

$$\Delta E = \sqrt{(L^* - L_o^*)^2 + (a^* - a_o^*)^2 + (b^* - b_o^*)^2}$$

wherein L* indicated lightness and a* and b* were the chromaticity coordinates of the highly sensitised colored locks whereas $L_o^*$ indicates the lightness and $a_o^*$ et $b_o^*$ were the chromaticity of the natural colored locks. The lower the value of ΔE, the weaker selectivity of the coloration and the more uniform the color of the hair along the fiber from the roots to the hair.

| Mixture | Hair type | L* | a* | b* | ΔE |
|---|---|---|---|---|---|
| A1 + B + C | BN | 33.74 | 35.17 | 24.73 | 8.70 |
| (comparative) | SA42 | 39.70 | 39.52 | 29.33 |  |
| A2 + B + C | BN | 35.30 | 37.63 | 26.39 | 5.15 |
| (inventive) | SA42 | 39.76 | 39.33 | 28.32 |  |

The mixture obtained with the composition A2 led to a color with a weaker selectivity, thus better, than the one obtained from the mixture obtained with the composition A1

Example 3

The following compositions were prepared (quantity expressed in g)

|  | A3 (comparative) | A4 (inventive) |
|---|---|---|
| isopropyle Myristate | 52 | 87 |
| Oleth-10 | 10 | 10 |
| Disteardimonium hectorite | 2.25 | 2.25 |
| propylene Carbonate | 0.75 | 0.75 |
| Water | 35 | — |

Composition B' (in g)

| copper sulphate of 2-(4,5-diamino-1H-pyrazol-1-yl ethanol | 3.4833 |
|---|---|
| m-aminophenol | 1.5805 |
| Hydroxyethyl cellulose (Natrosol 250 HHR) | 1.5 |
| Glycol Dipropylene | 3 |
| Glycol Hexylene | 3 |
| Propylene glycol | 6.2 |
| Monoethanolamine | 16.81 |
| Ethanol | 8.25 |
| Reducers, sequestering agents | Qs |
| Water | Qs 100 |

Composition C (in g)

| hydrogen Peroxide | 6 |
|---|---|
| cetearylic Alcohol | 2.28 |
| Ceteareth-25 | 0.57 |
| Glycerin | 0.5 |
| Trideceth-2 MEA carboxamide | 0.85 |
| Stabilisants, sequestering agents | Qs |
| phosphoric Acid | Qs pH = 2 |
| Water | Qs 100 |

At the time of use, 10 g of composition A3 and A4 were each separately mixed with 4 g of composition B' and 15 g of composition C.

Each mixture was then applied on locks of natural white 90% hair (BN) and of strongly sensitised hair (SA42), at the rate of 14.5 g of mixture for 1 g of hair. After a leave-on time of 30 minutes, the hair was rinsed, washed with a standard shampoo and dried.

The colour of the hair was determined by using the Datacolor SF600X Spectraflash (illuminant D65, angle 10°, specular components included).

The selectivity of the color was determined according to the method described above. The results are in the following table:

| Mixture | Type of hair | L* | a* | a* | ΔE |
|---|---|---|---|---|---|
| A3 + B' + C | BN | 27.81 | 26.65 | 10.85 | 3.54 |
| (comparative) | SA42 | 26.32 | 29.35 | 12.59 |  |
| A4 + B' + C | BN | 25.79 | 26.29 | 10.64 | 0.99 |
| (inventive) | SA42 | 24.84 | 26.51 | 10.80 |  |

The mixture obtained with the composition A4 led to a color with a weaker selectivity, thus better than the color obtained from a mixture obtained with the composition A3.

What is claimed is:

1. A ready-to-use composition for the oxidation dyeing of keratin fibers, comprising:
    A) at least one fatty substance present in the ready-to-use composition in an amount of greater than or equal to 25% by weight relative to the total weight of the ready-to-use composition,
    B) at least one oxidation base chosen from 4,5-diaminopyrazoles and the acid addition salts thereof,
    C) at least one dye precursor other than the at least one oxidation base defined in B),
    D) at least one oxidizing agent, and optionally
    E) at least one alkaline agent.

2. The ready-to-use composition according to claim 1, wherein the at least one fatty substance is chosen from compounds which are liquid and from compounds which are pasty at ambient temperature and at atmospheric pressure.

3. The ready-to-use composition according to claim 2, wherein the at least one fatty substance is chosen from compounds which are liquid at ambient temperature and at atmospheric pressure.

4. The ready-to-use composition according to claim 1, wherein the at least one fatty substance is other than fatty acid.

5. The ready-to-use composition according to claim 1, wherein the at least one fatty substance is chosen from lower alkanes, fatty alcohols, fatty acid esters, fatty alcohol esters, nonsilicone oils, nonsilicone waxes and silicones.

6. The ready-to-use composition according to claim 1, wherein the at least one fatty substance is non-silicone-based.

7. The ready-to-use composition according to claim 1, wherein the at least one 4,5-diaminopyrazole oxidation base is chosen from compounds of formula (I) and the acid addition salts thereof:

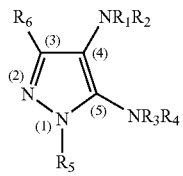

(I)

wherein:
$R_1$, $R_2$, $R_3$, $R_4$ and $R_5$, which may be identical or different, represent a hydrogen atom; or a $C_1$-$C_6$ alkyl radical which is unsubstituted or substituted with at least one substituent chosen from OR, with R, which may be identical or different, representing a hydrogen atom or an alkyl radical, and $R_6$ is a hydrogen atom or a $C_1$-$C_6$ alkyl radical.

8. The ready-to-use composition according to claim 1, wherein the at least one 4,5-diaminopyrazole oxidation base is chosen from 4,5-diamino-1-(2-hydroxyethyl)-1H-pyrazole and the acid addition salts thereof.

9. The ready-to-use composition according to claim 1, wherein the at least one dye precursor is chosen from oxidation bases other than 4,5-diaminopyrazoles, and couplers.

10. The ready-to-use composition according to claim 1, wherein the at least one dye precursor is chosen from ortho- and para-phenylenediamine oxidation bases, double bases, ortho- and para-aminophenols, heterocyclic bases and the acid addition salts thereof.

11. The ready-to-use composition according to claim 1, wherein the at least one dye precursor is chosen from para-aminophenol oxidation bases, heterocyclic bases and the acid addition salts thereof.

12. The ready-to-use composition according to claim 1, wherein the at least one dye precursor is chosen from meta-aminophenol couplers, meta-phenylenediamines, meta-diphenols, naphthols, heterocyclic couplers and the acid addition salts thereof.

13. The ready-to-use composition according to claim 12, wherein the at least one dye precursor is chosen from meta-aminophenol and meta-phenylenediamine couplers.

14. The ready-to-use composition according to claim 1, wherein the at least one oxidizing agent is a peroxide.

15. The ready-to-use composition according to claim 14, wherein the at least one oxidizing agent is hydrogen peroxide.

16. The ready-to-use composition according to claim 1, wherein the at least one alkaline agent is chosen from ammonia and alkanolamines.

17. The ready-to-use composition according to claim 16, wherein the at least one alkaline agent is chosen from alkanolamines.

18. A process for dyeing keratin fibers, comprising
applying to the keratin fibers for a period of time sufficient to develop the desired coloring, a ready-to-use composition, wherein the ready-to-use composition comprises
A) at least one fatty substance present in the ready-to-use composition in an amount of greater than or equal to 25% by weight relative to the total weight of the ready-to-use composition,
B) at least one oxidation base chosen from 4,5-diaminopyrazoles and acid addition salts thereof,
C) at least one additional dye precursor other than the at least one oxidation base defined in B),
D) at least one oxidizing agent, and optionally
E) at least one alkaline agent.

19. A multi-compartment kit, comprising
a first compartment containing a composition comprising at least one fatty substance,
a second compartment containing at least one oxidation base chosen from 4,5-diaminopyrazoles and acid addition salts thereof, at least one dye precursor other than the at least one oxidation base chosen from 4,5-diaminopyrazoles, and optionally at least one alkaline agent, and
a third compartment containing at least one oxidizing agent(s), and optionally at least one fatty substance.

20. A multi-compartment kit, comprising
a first compartment containing a composition comprising at least one fatty substance and at least one oxidizing agent, and
a second compartment containing at least one oxidation base chosen from 4,5-diaminopyrazoles and the acid addition salts thereof, at least one dye precursor other than the at least one oxidation dye chosen from 4,5-diaminopyrazoles, and optionally at least one alkaline agent.

21. A multi-compartment kit, comprising
a first compartment containing a composition comprising at least one fatty substance, at least one oxidation dye chosen from 4,5-diaminopyrazoles and acid addition salts thereof, at least one dye precursor other than the at least one oxidation dye chosen from 4,5-diaminopyrazoles, and at least one optional alkaline agent, and
a second compartment containing at least one oxidizing agent.

* * * * *